United States Patent [19]
Kumar et al.

[11] Patent Number: 5,821,351
[45] Date of Patent: Oct. 13, 1998

[54] PRODUCTION OF HEMOGLOBIN HAVING A DELTA-LIKE GLOBIN

[75] Inventors: Ramesh Kumar, Pennington; Ajay Sharma, Laurenceville; John S. Logan, Robbinsville, all of N.J.

[73] Assignee: DNX Biotherapeutics, Princeton, N.J.

[21] Appl. No.: 258,311

[22] Filed: Jun. 10, 1994

[51] Int. Cl.$^6$ .............................. C12N 15/06; C12N 5/00; C07H 21/04

[52] U.S. Cl. ...................... 536/23.4; 435/69.6; 435/69.7; 435/172.3; 536/23.4; 536/23.5; 800/2; 935/34

[58] Field of Search ................................. 536/23.1, 23.4, 536/23.5; 930/25; 935/34, 47; 435/69.6, 69.7, 172.3; 800/2

[56] References Cited

FOREIGN PATENT DOCUMENTS

| | | |
|---|---|---|
| WO 89/01517 | 2/1989 | WIPO . |
| WO 92/11380 | 7/1992 | WIPO . |
| WO 92/22644 | 12/1992 | WIPO . |
| WO 95/04744 | 2/1995 | WIPO . |

OTHER PUBLICATIONS

Gordon and Ruddle, 1981, "Integration and Stable Germ Line Transmission of Genes Injected into Mouse Pronuclei", *Science* 214: 1244–1246.

Gordon et al., 1980, "Genetic transformation of mouse embryos by microinjection of purified DNA", *Proc. Natl. Acad. Sci. USA* 77: 7380–7384.

Gordon et al., 1989, *Transgenic Animals, Int. Rev. Cytol.* 115: 171–229.

Kinderlerer, "Thermal Denaturation of Human Haemoglobin", *Proceedings of the Biochemical Society* 119: 66P–67P.

LaFlamme et al., 1987, "Expression of Chimeric Human β– and δ–Globin Genes During Erythroid Differentiation", *The Journal of Biological Chemistry* 262: 4819–4826.

Lauer et al., 1980, "The Chromosomal Arrangement of Human α–Like Globin Genes: Sequence Homology and α–Globin Gene Deletions", *Cell* 20: 119–130.

Lavitrano et al., 1989, "Sperm Cells as Vectors for Introducing Foreign DNA into Eggs: Genetic Transformation of Mice", *Cell* 57: 717–723.

Lawn et al., 1980, "The Nucleotide Sequence of the human β–Globin Gene", *Cell* 21: 647–651.

Li et al., 1985, "Nucleotide Sequence of 16–Kilobase Pairs of DNA 5' to the Human ε–Globin Gene", *J. Biol. Chem.* 260: 14901.

Li et al., 1990, "β–globin locus activation regions: Conservation of organization, structure and function", *Proc. Natl. Acad. Sci.* 87: 8207.

Li et al., 1991, "Primary Structure of the Goat β–Globin Locus Control Region", *Genomics* 9: 488.

Liebhaber et al., 1980, "Cloning and complete nucleotide sequence of human 5'–α–globin gene", *Biochemistry* 77: 7054–7058.

Lo, 1983, "Transformation by Ionotophoretic Microinjection of DNA: Multiple Integrations Without Tandem Insertions", *Mol. Cell. Biol.* 3: 1803–1814.

Margot et al., 1989, "Complete Nucleotide Sequence of the Rabbit α–like Globin Gene Cluster", *J. Mol. biol.* 205: 15–40.

(List continued on next page.)

*Primary Examiner*—Brian R. Stanton
*Attorney, Agent, or Firm*—Joseph B. Barrett

[57] ABSTRACT

The present invention concerns a method and compositions of matter useful for the method of making, in transgenic animals, a human hemoglobin that is more stable and more readily purified from the endogenous hemoglobins of the transgenic animal than hemoglobin A. The hemoglobins produced by the invention include hemoglobin $A_2$, which is an $\beta_2\delta_2$ tetramer, as well as other hemoglobins having similar properties to hemoglobin $A_2$ and have β/δchimeric globins. The specification discloses a chimeric gene, encoding a human δ-globin that is expressed in transgenic animals at levels approximating the level of expression of the α or β globin.

1 Claim, 3 Drawing Sheets

OTHER PUBLICATIONS

O'Neill et al., 1988, "Transcription Factor OTF–1 Is Functionally Identical to the DNA Replication Factor NF–III", *Science 241*: 1210–1213.

Ogden et al., 1992, "Expression and Assembly of Functional Human Hemoglobin in *S. Cervisiae*", *Biomaterials, Artifical Cells & Immobilization Technology 20*: 473–475.

Perutz and Raidt, 1975, "Sterochemical basis of heat stability in bacterial ferredoxins and in haemoglobin A2", *Nature 255*: 256–259.

Plumb et al., 1989, GATAAG; a cis–control region binding an erythroid–specific nuclear factor with a role in globin and non–globin gene expression, *Nucleic Acids Research 17*: 73–93.

Pruijn, 1987, "Promoter and Enhancer elements containing a conserved sequence motif are recognized by nuclear factor III, a protein stimulating adenovirus DNA replication", *The EMBO Journal 6*: 3771–3778.

Schroeder et al., 1973, An Individual with "Miyada"–Like Hemoglobin Indistinguishable form Hemoglobin $A_2$, *Biochemfical Genetics 10*: 135–147.

Shehee et al., 1989, "Nucleotide Sequence of the BALB/c Mouse β–Globin Complex" *J. Mol. Biol. 205*: 41.

Spritz et al., 1980, "Complete Nucleotide Sequence of the Human δ–Globin Gene", *Cell 21*: 639–646.

Steinberg et al., 1982, "Beta–thalassemia with exceptionally high hemoglobin $A_2$", *J. Lab. Clin. Med. 100*: 548–557.

Thompson et al., 1989, "Germ Line Transmission and Expression of a Corrected HPRT Gene Produced by gene Targeting in Embryonic Stem Cells", *Cell 56*: 313–321.

Van Der Putten, 1985, "Efficient insertion of genes into the mouse germ line via retroviral vectors", *Proc. Natl. Acad. Sci. USA 82*: 6148–6152.

Wall et al., 1988, "The human β–globin gene 3' enhancer contains multiple binding sites for an erythroid–specific protein", *Genes & Development 2*: 1089–1100.

Wood et al., 1978, "Human Globin Gene Expression: Control of β,δ and δβ Chain Production", *Cell 15*: 437–446.

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: NO

( i v ) ANTI-SENSE: NO

( x i ) SEQUENCE DESCRIPTION: SEQ ID NO:1:

GGTGAATTCT TTGCCAAAGT TACGGGCCAG CAC           33

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: NO

( i v ) ANTI-SENSE: NO

( x i ) SEQUENCE DESCRIPTION: SEQ ID NO:2:

GTGGATCCTG AGAACTTCAG           20

( 2 ) INFORMATION FOR SEQ ID NO:3:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: NO

( i v ) ANTI-SENSE: NO

( x i ) SEQUENCE DESCRIPTION: SEQ ID NO:3:

ATTTAGGTGA CACTAGAGAA TC           22

( 2 ) INFORMATION FOR SEQ ID NO:4:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: NO

-continued (iv) ANTI-SENSE: NO (xi) SEQUENCE DESCRIPTION: SEQ ID NO:4:

AAAGAATTCA CCCCACAGAT GCAGGCTGCC 30

PRODUCTION OF HEMOGLOBIN HAVING A DELTA-LIKE GLOBIN

1. FIELD OF THE INVENTION

The present invention concerns the production of human hemoglobin in animals other than humans. The hemoglobin is to be used as a blood substitute, thus avoiding the disadvantages of obtaining human blood donors. More particularly, the present invention concerns novel nucleic acid molecules that can be used to construct transgenic animals that will produce large amounts of human α-globin and δ-globin. These animals are a source of Hemoglobin $A_2$, which contains two α and two δ-chains in place of the two α and two β-chains found in the most common adult hemoglobin, Hemoglobin A.

2. BACKGROUND TO THE INVENTION

Oxygen is absorbed through the lungs and carried by hemoglobin in red blood cells (RBC) for delivery to tissues throughout the body. At high oxygen concentrations, such as those found in the proximity of the lungs, oxygen binds to hemoglobin, but is released in areas of low oxygen concentration, where it is needed.

Each hemoglobin molecule in an adult consists of two α-globin subunits and two β- or δ-globin subunits or chains. The globin chains themselves are synthesized from templates, called mRNAs which are, in turn, synthesized from a master template which is the globin gene. The gene contains three regions (exons) which code for the amino acids of the globin and contains other regions, called intervening sequences (IVS), that are transcribed, but then removed from the primary transcript when the mature mRNA is formed. The mature mRNA is then translated into the globin protein.

Each globin chain contains an iron atom coordinated by the two imidazole nitrogens of two histidines. The iron atom is surrounded by a protoporphyrin ring which is contained within the hemoglobin molecule but not chemically linked to it. The protoporphyrin and the iron atom together form a heme group which binds the oxygen molecule and of course, gives hemoglobin its name. Thus, each hemoglobin tetramer is capable of binding four molecules of oxygen. Hemoglobin that contains two α-globin chains and two β-globin chains is called Hemoglobin A (HbA); the other form of adult hemoglobin, which has two δ-globin chains is termed $HbA_2$. Both types of hemoglobins are synthesized in the same cells, called erythrocyte precursors, which, as they mature become recticulocytes, and finally become erythrocytes or red blood cells (RBC). Normally only about 2.0–2.5% of the hemoglobin will be $HbA_2$, although persons having a genetically defective β-globin gene are known to express as much as 15% $HbA_2$. Schroeder, W. A., et al., 1975, BIOCHEM. GENET. 10:135; Steinberg, M. H., et al., 1982, J.LAB.CLIN.MED. 100:548. No hemoglobin has both a β and a δ chain.

Many medical and surgical conditions require the administration of whole blood or of the RBC fraction of blood (packed RBC). At present the only sources of RBC suitable for clinical use are human donors. It is, however, expensive to procure human blood in the quantities required. Moreover, even when an adequate amount of blood is obtainable there are many risks associated with the transfusion of blood from one individual to another. The avoidance of these risks entails yet more expense and the efforts of highly trained medical practitioners, which, even though prodigious, are not completely successful. Transfusion reactions and blood-born infections remain a substantial and significant risk. The risks of transfusion and limited availability of blood deter physicians from using blood replacements in all but the most necessary cases.

Therefore, it would be highly desirable to be able to use manufactured hemoglobin as a blood substitute rather than obtain blood from human volunteers. Because the function of hemoglobin is entirely independent of the RBC, the hemoglobin derived from transgenic animals could be used as a blood substitute with only slight modifications such as cross-linking, Ogden, J. E., et al., 1992, BIOMATERIALS, ARTIFICAL CELLS & IMMOBILIZATION TECHNOLOGY 20: 473. The preferred type of hemoglobin for this purpose is $HbA_2$. $HbA_2$ is more stable than HbA, Kinderlerer, J., et al., 1970, BIOCHEM.J. 119:66P, which would allow for a longer life-span of the product and would also allow the use of harsher conditions during the manufacture of the synthetic product. Secondly, the physicochemical differences between $HbA_2$ and the HbAs of other animals are larger than between human HbA and the non-human HbAs. Therefore, the process of purifying the desired human Hb from other types of hemoglobins is significantly easier.

The efforts directed towards the production of human globin chains and HbA in transgenic animals have been considerable. See, e.g., Logan et al., WO92/22646, Holis et al., WO92/11380, and Grosveld, F., WO89/01517, which are hereby incorporated by reference in their entirety. However, the application of these same methods to the production of δ-globin have been unsuccessful.

Prior to the present application, there have been studies directed towards understanding the reasons for the poor production of the δ-globin chain compared to β-globin. Wood et al., 1978, CELL 15:437, found that there were substantial differences between β- and δ-globin at all stages of the synthetic process. Those workers reported that the rates of synthesis and of processing of the primary δ-globin transcripts were less than that of β-globin; that the life-time of the mature transcript was shorter and that the rate of translation of δ-globin was less than that of β-globin. One explanation of the reason for these differences may be the particular nucleotide sequences (codons) used to encode each amino acid. Spritz, R. A., et al., 1980, CELL 21:639, reports that at least two of the codons used in human δ-globin are not used in other globins.

More recently, LaFlamme et al., 1987, J.Biol.Chem. 262:4819, considered the production of human δ-globin mRNA in a transfected mouse erythroleukemia cell line, which was induced to produce quantities of globins. LaFlamme's studies concerned the effects on the production of δ-globin mRNA of the intervening sequences, the portions of the gene between the sequences that encode the globin protein. Each globin gene has two regions of intervening sequences (IVS), sequences that are removed from the primary transcript also known as introns. LaFlamme et al. exchanged the longer IVSs of the β and δ genes, called βIVS-2 and δIVS-2, respectively, with the IVSs of the heterologous globin gene. They found that while the introduction of the δIVS-2 into the β-globin gene had a significant negative effect on the production of β-globin mRNA, the substitution of βIVS-2 into the δ-globin gene did not increase δ-globin mRNA production to any appreciable extent.

3. SUMMARY OF THE INVENTION

The present invention concerns a chimeric globin gene expression cassette wherein the control elements, i.e., the Locus Control Region, the promoter, the 5' and 3' untranslated portion of the mature message and the longer intervening sequence are all derived from a globin gene which encodes a major globin product, such as α or β globin. However, the coding sequences of the chimeric gene encodes human δ globin. Transgenic animals having incorporated the chimeric gene of the invention and a human α-globin gene linked to it make large quantities of human Hemoglobin A$_2$. More particularly, the invention provides: the chimeric gene comprising exons encoding human δ globin but having a promoter and untranslated segments from an a or β globin gene; the expression cassette comprising the above described chimeric gene and a suitable globin Locus Control Region (LCR); a transgenic animal expressing the cassette; and erythrocytes from the transgenic animals and methods of purifying Hemoglobin A$_2$ from the erythrocytes.

5. DETAILED DESCRIPTION OF THE INVENTION

The present invention involves the production of human Hemoglobin A$_2$ (HbA$_2$) in transgenic animals. In particular, the invention involves a chimeric gene to encode human δ-globin. In this chimeric gene the exons that encode δ-globin replace the exons of a gene that encodes a major component of the hemoglobin of an adult, i.e., an α or a β globin gene. The sequence of the human β- and δ-globin genes are known. Lawn, R. M. et al., 1980, CELL 21:647–651; Spritz, R. A., et al., 1980, CELL 21:639–642 (which are hereby incorporated by reference). The sequences and organization of the human α-globin genes are also known. Lauer, J., et al., 1980, CELL 20:119–130; Liebhaber, S. A., et al., 1980, Proc.Natl.Acad.Sci. 77:7054–58 (which are hereby incorporated by reference).

Thus, primary transcript of the chimeric gene of the invention differs from that of the δ-globin gene in that the longer intervening sequence of the δ-globin gene (δIVS-2) is replaced by at least a portion IVS-2 of a major globin and in one embodiment by the entire IVS-2 of an α-globin gene or a β-globin gene. However, the smaller intervening sequence (δIVS-1) can be derived from either the δ IVS-1 or IVS-1 from a major globin gene. The gene of the invention further has a promoter of an α-globin gene or a β-globin gene, and, in one embodiment, also has the 3' and 5' untranslated regions are derived from a major globin sequence.

The IVS-2 of β-globin but not of δ-globin contains three binding sites for the erythroid specific transcription factor NF-E1. The sites can have any of the sequences: 5' GATAAG3' or 5'(T/A)GATA(G/A)3' or their complements, hereinafter any of these sequences are termed a "GATA-1" site. Wall, L., et al., 1988, GENES DEVEL. 2:1089–1100; Plumb, M., et al., 1989, Nucl.Acid.Res. 17:73–92. There is also a site for binding the general transcription factor, NF-III, which can be the sequence 5'ATTTGCAT3' or its complement, hereinafter an "Oct-1" site. Pruijn, J. M., et al., 1987, EMBO J. 6:3771–78; O'Neill, E. A., et al., SCIENCE 241:1210–13. Thus, the genes within the scope of the invention have one or two Oct-1 sites, preferably one, and between two and six, preferably three, GATA-1 sites disposed between the splice donor and splice acceptor sites that define the intron or intervening sequence.

The chimeric genes of the invention are used to engineer transgenic animals that express the chimeric gene and a normal α-globin gene in erythroid cells so that a hemoglobin similar to human HbA$_2$ and useful as a blood substitute is produced. See, e.g., U.S. Patent Application, Logan et al., U.S. patent application Ser. No. 08/105,989, filed Aug. 11, 1993, which is hereby incorporated by reference. After bleeding of the transgenic animal, the human HbA$_2$ can be readily separated from the hemoglobin of the host animals for use as a blood substitute.

5.1 Description of the Proteins Encoded by the Gene of the Invention

The sequences of the human globins and the homology of their positions is given in HEMOGLOBIN: MOLECULAR, GENETIC AND CLINICAL ASPECTS by H. F. Bunn & B. G. Forget (W. B. Saunders & Co. Phil.) Table 4-2, which is herewith incorporated by reference. The human δ-globin of HbA$_2$ differs from the more familiar human β-globin of HbA at only 10 residues out of 146. Spritz et al., 1980, CELL 21:639. A process of gene conversion results in parallel evolution of β and δ-globin genes.

Of the 10 differences three are of significance for the present invention. The Glu$^{22}$ and the adjacent His$^{116,117}$ of β-globin are replaced, in δ-globin, by Ala, Arg and Asn respectively. These substitutions lead to two significant changes. Firstly, there is an additional interaction between the α and δ globin chains, specifically between δArg$^{116}$ and αPro$^{114}$, which confers additional stability to the HbA$_2$ molecule. Perutz, M. and Raidt, H., 1975, NATURE 255:256.

Secondly, the net effect of the substitutions on the charge of the hemoglobin is the replacement of a Glu by an Arg. This substitution changes the isoelectric point of HbA$_2$ by roughly 0.5 pH unit from that of HbA, i.e., from pI=6.95 of HbA to pI=7.40 of HbA$_2$. The more basic isoelectric point allows for the separation of HbA$_2$ from the blood of the transgenic animal more readily than the β-globin containing HbA.

The proteins encoded by the gene of the present invention, thus, encompass globins that are homologous to either β- or δ- globin at every position except at 22 and 116 where a different tests apply: at position 22, the residue is uncharged at physiologic pH and at position 116, an arginine is present. A globin meeting these conditions is termed a δ-homologous globin hereinafter. In addition, in the preferred embodiment of the invention, the hemoglobin having two δ-homologous globins and two human α-globins has a pI of between 7.3 and 7.5; a δ-homologous globin that forms such a hemoglobin is referred to hereinafter as a "δ-like globin." In a preferred embodiment, the δ-like globin is homologous to human β or δ globin at all positions except for 22 and 116 will be referred to as a human δ-like globin. In the most preferred embodiment of the invention the human δ-like globin is human δ-globin.

The scope of the invention includes the placement of the chimeric gene in a vector constructed for the generation of transgenic animals. The vector is designed to direct expression of the chimeric globin gene in erythropoietic cells of the animal. To this end the vector should further contain a globin Locus Control Region from a major globin locus, i.e. the α-globin or β-globin locus, and a human α-globin gene operably linked to a promoter.

The production of the high levels of transgenic Hemoglobin $A_2$ that are taught by the invention is accomplished, in part, through a locus control region (LCR). The structure of many LCR of the β-globin genes have been published, e.g., human, Li, Q., et al., 1985, J.Biol.Chem. 260:14,901; Li. Q., et al., 1990, PROC.NATL.ACAD.SCI. 87:8207; mouse, Shehee, W. R., et al., 1989, J.MOL.BIOL. 205:41; rabbit, Margot, J. B., et al., 1989, J.MOL.BIOL. 205:15; and goat, Li, Q., et al., 1991, GENOMICS 9:488, each of which are incorporated by reference herein. The structure of the pig LCR is reported in a co-assigned U.S. Patent Application, Logan et al., U.S. patent application Ser. No. 08/105,989, filed Aug. 11, 1993, which is hereby incorporated by reference.

A shortened LCR which is suited for use with the present invention has been constructed and contains only the DNase super-hypersensitive regions of the human β-globin locus control region (hereinafter "$\mu\beta$LCR"). This 6.5 kb LCR consists of four fragments of between 1.1 kb and 2.1 kb, and has been shown to be active in an orientation independent manner in transfected mouse erythroleukemia cells. The detailed structure of the $\mu\beta$LCR is provided in Grosveld, F. G., 1989, WO 89/01517 and 1992, WO 92/11380 which are hereby incorporated by reference in its entirety.

The chimeric globin gene encoding a δ-like globin and the vectors to be used in accordance with the invention can be constructed using recombinant DNA techniques well known to those skilled in the art, e.g., see Sambrook et al., 1989, Molecular Cloning: A Laboratory Manual, Cold Spring Harbor Press, Cold Spring Harbor, N.Y. The chimeric gene of the present invention can also be synthesized in whole or in part by a combination of readily available techniques. Such techniques include solid-phase nucleotide synthesis to construct primers containing new restriction sites, polymerase chain reaction amplification using such primers, to readily obtain fragments containing δ globin gene sequences for insertion into an isolated major globin gene and recombinant DNA techniques for the insertion of the fragments into the major globin gene and for production of the chimeric gene and the vectors for constructing the transgenic animals.

5.2 Generation of the Transgenic Animals

The invention provides the above-described chimeric nucleic acid which has been made substantially free of proteins, as by (for example) the well known chloroform/phenol extraction procedure or its equivalent. The invention also contemplates the above-described chimeric gene which has been introduced into any organism. Examples of such organisms would include plasmid cloning vectors and expression vectors suited for the production of the nucleic acid of the invention in bacterial hosts; eukaryotic expression systems such as erythroleukemia cell lines that can be induced to differentiate and to produce hemoglobin as well as constitutive, non-inducible eukaryotic expression systems.

The invention further contemplates that the above-described α-globin/δ-like globin chimeric gene expression cassette can be placed into the genome of a non-human animal. The invention further contemplates that the transgenic animals of the invention can be constructed by any of the available methods including pronuclear injection and transfection of embryonic stem cells followed by blastocyst fusion to create chimeric animals. The offspring of the chimeric animals are transgenic animals.

Animals of any species, including but not limited to mice, rats, rabbits, guinea pigs, pigs, micro-pigs, and non-human primates, e.g., baboons, squirrel monkeys and chimpanzees can be used to generate the transgenic animals of the invention so long as a known globin LCR is functional in that species. The preferred embodiments employ mice and pigs. Any technique known in the art can be used to introduce the transgene into animals to produce the founder lines of transgenic animals. Such techniques include, but are not limited to pronuclear microinjection (Gordon et al., 1980, PROC. NATL. ACAD. Sci. USA 77: 7380–7384; Gordon & Ruddle, 1981, SCIENCE 214: 1244–1246; U.S. Pat. No. 4,873,191 (Oct. 10, 1989) T. E. Wagner and P. C. Hoppe); retrovirus mediated gene transfer into germ lines (Van der Putten et al., 1985, PROC. NATL. ACAD. Sci. USA 82: 6148–6152); gene targeting in embryonic stem cells (Thompson et al., 1989, CELL 56: 313–321); electroporation of embryos (Lo, 1983, MOL. CELL. BIOL. 3: 1803–1814); and sperm-mediated gene transfer (Lavitrano et al., 1989, CELL 57: 717–723); etc. For a review of such techniques, see Gordon, 1989, Transgenic Animals, INTL. REV. CYTOL. 115: 171–229, which is incorporated by reference herein in its entirety). Once the founder animals are produced, they can be bred, inbred, crossbred or outbred to produce colonies for the production of $HbA_2$ according to the present invention.

The present invention provides for transgenic animals that carry the transgene in all their cells, as well as animals which carry the transgene in some, but not all cells, i.e., mosaic animals. The transgene can be integrated as a single transgene or in tandem, e.g., head to head tandems, or head to tail or tail to tail.

5.3 Isolation and Characterization of the Chimeric Gene Product

The human $HbA_2$ is superior to human HbA for use in the manufacture of a blood substitute. The superiority can be readily appreciated from the study of the differences in primary structures of the β and δ globin genes. The $Glu^{22}$ and adjacent $His^{116,117}$ of β-globin are replaced in δ-globin by Ala, Arg and Asn respectively. These substitutions lead to two significant changes. Firstly, there is an additional interaction between the α and δ globin chains, specifically between $\delta Arg^{116}$ and $\alpha Pro^{114}$, which confers additional stability to the $HbA_2$ molecule. Perutz, M. and Raidt, H. , 1975, NATURE 255:256. Secondly, the alteration in the amino acid composition of the proteins changes the isoelectric point of Hemoglobin A by roughly 0.5 pH unit, from 6.95 to the 7.40 of $HbA_2$.

The practical consequence of the difference is that the purification $HbA_2$ can be much more readily accomplished by ion-exchange chromatography because, at physiologic pH, $HbA_2$ is the first hemoglobin to elute from the ion exchange resin used for the preparation of $HbA_2$ from transgenic hemolysate. e.g., Mono-P®, (Pharmacia), DEAE Cellulose (Whatman), Maenprep® (Biorad). In a preferred embodiment, the large scale purification of the $HbA_2$ is accomplished by application of the hemoglobin mixture to a Mono-P® ion exchange column or its equivalent in a buffer, which is about 10 mM NaCl, which will allow only the HbA$_2$ to pass through the column without binding.

5.4 Use of the δ-Like Globin Containing Hemoglobin

The hemoglobin made and purified according to the invention can then be polymerized by means well known to those in the art, dissolved in a physiological buffer using pharmaceutically acceptable water and salts. The solution of between about 2.5 and 100 mg/ml of protein is then administered intravenously by means and at doses selected to restore the subjects blood volume and/or hemoglobin concentration. The following United States Patents concern part or all of these processes and are hereby incorporated by reference. U.S. Pat. Nos. 5,234,903; 5,194,590; 5,084,558; 5,079,337; 4,900,816; 4,826,811; 4,777244 and 4,698,387.

6. WORKING EXAMPLES

6.1 Construction of Hemoglobin A$_2$ Expression Vector #534

A two step cloning procedure was employed. In step 1 a chimeric δ/β globin gene was created by a PCR based cloning strategy. There are only four amino-acid changes between β and δ globin proteins in the region of amino acid residues 110 to 146 encoded by DNA sequences located between unique Bam H1 and Eco R1 restriction enzyme sites in plasmid pSelectβ (ATCC Accession No. 75782).

We employed a degenerate 3' PCR primer δ 116/117 (5' GGT GAA TTC TTT GCC AAA GTT ACG GGC CAG CAC3', where the Eco R1 site is shown underlined and the anti-sense sequence of codons changed from the β globin sequence to a δ globin sequence are shown in bold) and a 5' PCR primer 2B5 (located in the second exon of β globin and coinciding with the Bam H1 site, (5' GTG GAT CCT GAG AAC TTC AG 3') were used to amplify ~1 Kbp fragment using pSelectβ as a template. This fragment was digested with Bam H1 and Eco R1 to obtain fragment δA. δA contains sequences of the β globin 2nd exon, 2nd intron and part of the 3rd exon where the sequences encoding residues 116 and 117 were converted to the δ globin sequence.

Using 3' PCR primer from the SP6 plasmid (5' ATT TAG GTG ACA CTA GAG AAT C3') and another degenerate 5' PCR primer δ125/126 (5' AAA GAA TTC ACC CCA CAG ATG CAG GCT GCC 3') where the Eco R1 site is again shown underlined and the sense sequence of codons changed from the β globin sequence to a δ globin sequence are shown in bold, a ~2 Kbp fragment was amplified using pSelectβ as a template. This fragment was digested with Eco R1 and Mlu 1 to obtain δB which contains the 3rd exon of β globin with codons 125 and 126 converted to the δ globin sequence, the β globin gene 3' UTR and downstream sequences.

The remaining portions of the δ globin genomic coding sequences were obtained by digestion of plasmid pSelectβpδ with Nco 1 and Bam H1. The three fragments described above were ligated into Nco 1 and Mlu 1 digested plasmid pSelectβ to create plasmid pSelectβpδ with β intron and β3'.

Step 2: The modified chimeric δ globin gene was obtained as a Kpn 1 and Mlu 1 fragment and cloned into similarly digested pLCRαε. The resultant plasmid pLCRαεδ* was designated construct 534 (deposited as ATCC Accession No. 75785) from which an Sst 2 to Mlu 1 fragment was obtained for microinjection.

6.2 Production of Transgenic Mice

Transgenic mice were created by the pronuclear microinjection technique as described in B. Hogan, F. Constantini and E. Lacy, 1986, MANIPULATING THE MOUSE EMBRYO, A LABORATORY MANUAL, (Cold Spring Harbor Press) and U.S. Pat. No. 4,873,191. The percent HbA$_2$ in hemolysates of 8 animals was determined as shown in Table 1 below. The results show HbA$_2$ up to levels of about 20% of the total hemoglobin.

TABLE 1

| Expression of human HbA$_2$ By Construct 534 Transgenics | | | |
|---|---|---|---|
| Animal | Sex | Generation | Hb A2(%) |
| 9-1 | F | G0 | 15.08 |
| 9-1-1 | F | F1 | 7.69 |
| 9-1-2 | F | F1 | 18.81 |
| 9-1-13 | F | F2 | 7.65 |
| 13-1 | F | G0 | 6.92 |
| 13-2 | F | G0 | 2.23 |
| 20-2 | F | G0 | 8.33 |
| 20-3 | M | G0 | 5.22 |

Figure 1A:
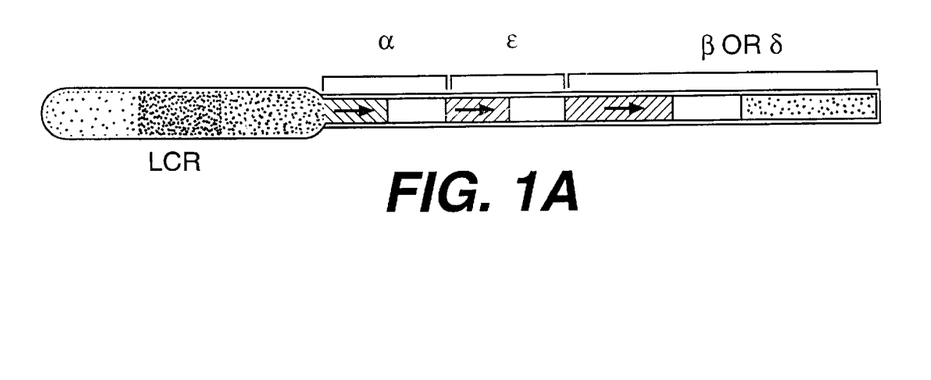
FIGS. 1A and 1B. A: The overall organization of a construct suitable for transfection into a transgenic animal having a Locus Control Region (LCR) with promoters and structural genes for the α, ε and β or δ globin. B: A schematic illustrating the placement of exons I, II and III (broader rectangles) of the human δ-globin gene into a human β-globin gene having intervening sequences (narrower rectangles). The nucleotide length of each region is superposed.
Figure 1B:
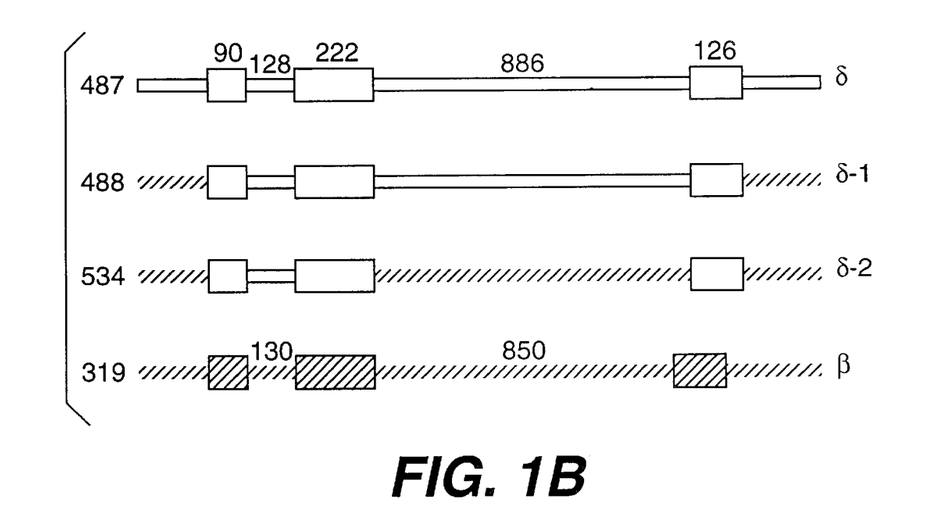
Figure 2:
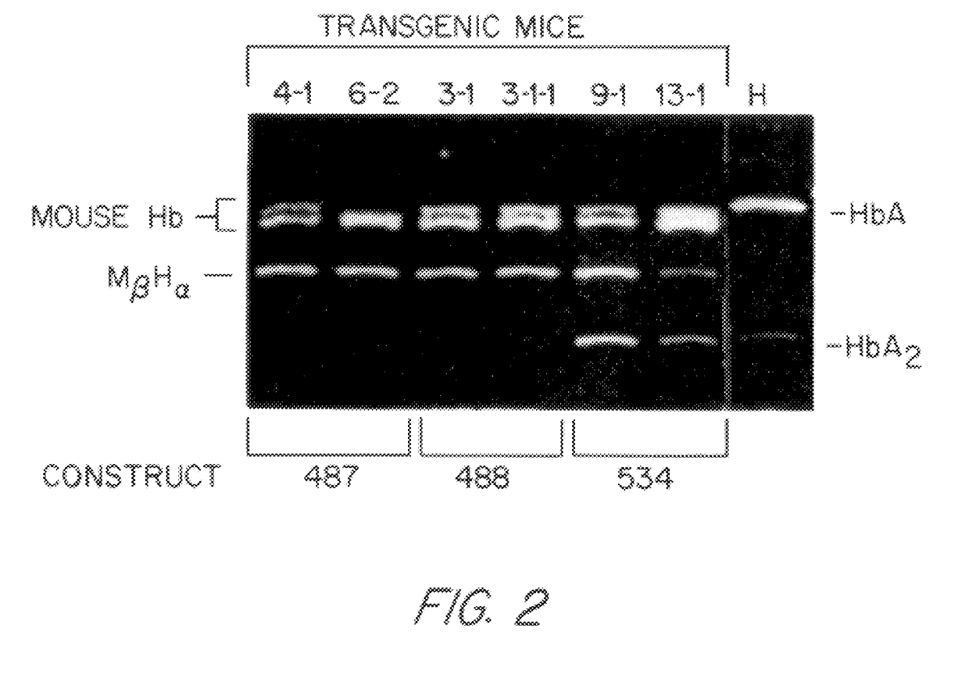
FIG. 2. Isoelectric Focusing (IEF) analysis of hemolysates of six transgenic mice.
Figure 3A:
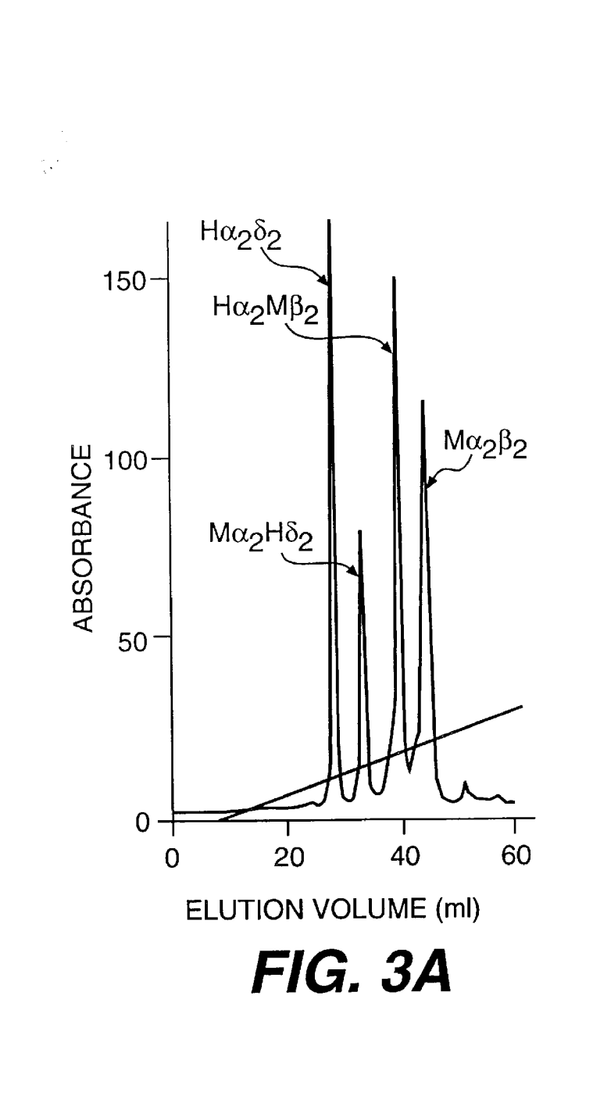
FIGS. 3A and 3B. A: Chromatogram of the proteins of a hemolysate of a transgenic mouse produced according to the invention eluted from a Mono P® ion exchange column by a linear NaCl gradient. Inset: IEF of peaks of the chromatogram. B: Chromatogram of proteins from the hemolysate of a transgenic mouse producing human HbA.
Figure 3B:
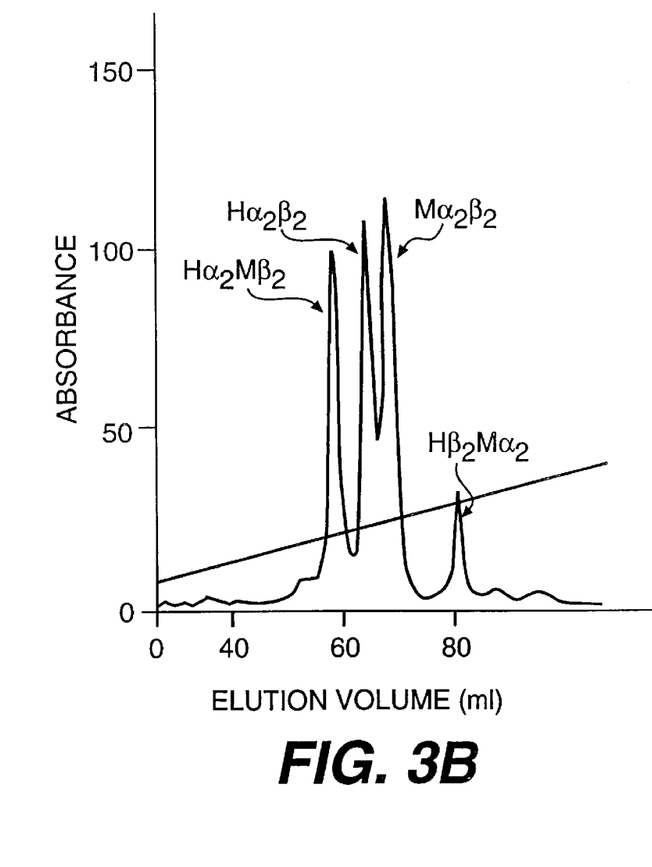

Transgenic animals were engineered using a human δ-globin gene (Construct # 487, FIG. 1B) or a chimeric gene consisting of sequences encoding a δ-globin exons and introns and β-globin 3' and 5' untranslated regions and promoter (Construct # 488, FIG. 1B). As shown in FIG. 2, transgenic animals having constructs # 487 and # 488 had barely detectable levels of HbA$_2$. By contrast, transgenic animals having Construct # 534 have readily detectable levels of HbA$_2$ by this analysis.

6.3 Purification of Hemoglobin A$_2$ From a Transgenic Mouse

Approximately 3 mg of hemolysate derived from mouse 534-9-1-1 was applied on a 4 ml Mono P® (Pharmacia, Piscataway, N.J.) column equilibrated with buffer A (10 mM Tris-Cl, pH 8.1, 20 mM Glycine). At a flow rate of 1 ml/min, five fractions were collected by sequentially eluting with a step-gradient of 20 ml each of the above buffer having and 5 mM, 10 mM, 15 mM, 20 mM, 25 mM, NaCl. Fractions were analyzed by isoelectric focussing on a pH 6–8 gradient (FIG. 2). Hemoglobin A$_2$ eluted in the first peak at greater than 95% purity. The second through fifth peaks contained HαMβ hybrid, MαAδ, mouse hemoglobin and modified hemoglobins, respectively.

The present invention is not to be limited in scope by the specific embodiments described which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

7. DEPOSIT OF MICROORGANISMS

A Construct #534 containing plasmid was deposited with the American Type Culture Collection (ATCC), 12301 Parklawn Drive, Rockville, Md. 20852 on May 23, 1994 as Accession No. ATCC 75785.

The present invention is not to be limited in scope by the specific embodiments described which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the claims.

What is claimed is:

1. A chimeric human globin gene identified as construct #534 which has been deposited at the American Type Culture Collection and which bears ATCC Accession No. 75785.

* * * * *